(12) United States Patent
Fleischer et al.

(10) Patent No.: US 7,364,749 B1
(45) Date of Patent: *Apr. 29, 2008

(54) PREPARATIONS FOR THE APPLICATION OF ANTI-INFECTIVE AND/OR ANTI-INFLAMMATORY AGENTS

(75) Inventors: Wolfgang Fleischer, Ingelheim (DE); Karen Reimer, Hambach (DE)

(73) Assignee: Euro-Celtique, S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 09/979,198

(22) PCT Filed: May 25, 2000

(86) PCT No.: PCT/EP00/04782

§ 371 (c)(1),
(2), (4) Date: Mar. 1, 2002

(87) PCT Pub. No.: WO00/72822

PCT Pub. Date: Dec. 7, 2000

(30) Foreign Application Priority Data

May 27, 1999 (DE) ................................. 199 24 312

(51) Int. Cl.
*A61K 9/127* (2006.01)
(52) U.S. Cl. .......................... 424/450; 424/45; 424/46; 424/47; 424/489
(58) Field of Classification Search ................ 424/450, 424/401, 484–502; 514/886, 887
See application file for complete search history.

(56) References Cited

U.S. PATENT DOCUMENTS 5,942,245 A   8/1999 Katinger et al.
2006/0116713 A1* 6/2006 Sepetka et al. ............. 606/200

FOREIGN PATENT DOCUMENTS

| CA | 1323568 | 9/1992 |
|---|---|---|
| CA | 2204493 | 4/1994 |
| CA | 2215716 | 9/1997 |
| CA | 2 332 389 | 5/1999 |
| EP | 0 267 050 | 5/1988 |
| JP | 02-204413 | 8/1990 |
| WO | WO 85/00112 | 1/1985 |
| WO | WO 87/07502 | 12/1987 |
| WO | WO 88/01862 | 3/1988 |
| WO | WO 91/16882 | 11/1991 |
| WO | WO 92/13873 | 8/1992 |
| WO | WO 93/24165 | 12/1993 |
| WO | WO 96/19199 | 6/1996 |
| WO | WO 96/22764 | 8/1996 |
| WO | WO 96/35435 | 11/1996 |
| WO | WO 98/05340 | 1/1999 |
| WO | WO00/72822 A1 | 12/2000 |

OTHER PUBLICATIONS

Bonowitz et al., 2001, "Comparative therapeutic and toxic effects of different povidone iodine (PVP-I) formulations in a model of oral candidosis based on in vitro reconstituted epithelium," J. Drug Targeting 9(1):75-83.
Brogmann et al., "Liposomal PVP-iodine eye drops—A new drug delivery system for an approved active ingredient," p. 52.
Damour et al., 1992, "Cytotoxicity evaluation of antiseptics and antibiotics on cultured human fibroblasts and keratinocytes," Burns 18(6):479-485.
Ganzer et al., 2001, Arthroskopie 14:31-44.
Ganzer et al., "Efficacy and tolerability of povidone-iodine liposome complex in infected knee joints of rabbits," p. 262, Abstract P1249.
Gottardi, 1991, "Iodine and iodine compounds," Disinfection, Sterilization, and Preservation, Fourth Ed., Lea & Febiger, Philadelphia pp. 152-156.
Hauser et al., 2001, "Liposomal PVP-iodine hydrogel improves epithelialization of meshed skin grafts—evaluation of the combined effects of moisture and antisepsis," The Plastic Surgery Research Council 46th Annual Meeting Jun. 9-12, Milwaukee, WI Clinical Microbiology and Infection 7(Supp 1):36.346.
Kiss et al., 1994, "Toxic effects of heavy metals on ionic channels," Pharmacol. Rev. 46(3):245-267.
Mayer et al., 1993, "Povidone-iodine and wound healing: A critical review," Wounds: A Compendium of Clinical Research and Practice 5(1):14-23.
Moren et al., eds., 1993, Aerosols in Medicine. Principles, Diagnosis, and Therapy pp. 70-83, 117-156.
Reimer et al., 2000, "In vitro and in vivo investigations of an innovative topical drug formulation for infection treatment and wound healing: Povidone iodine liposome hydrogel," Clinical Microbiology and Infection 6(Supp. 1):134-135, Abstract WeP230.

(Continued)

*Primary Examiner*—Gollamudi S. Kishore
(74) *Attorney, Agent, or Firm*—Jones Day

(57) ABSTRACT

Use of an anti-infective and/or anti-inflammatory agent for the preparation of a pharmaceutical composition for the treatment of diseases of external or internal parts of the human or animal body which are susceptible to the administration of such agents.

18 Claims, No Drawings

OTHER PUBLICATIONS

Reimer et al., 2000, "Povidone-iodine liposome complex," Hyg. Med. Jahrgang Supp. 1:16.15-17.00.

Reimer et al., 1999, "Povidone-iodine liposome complex—a novel anti-infective for topical treatment," Clin. Microbiol. Inf. 5(supp 3):136 Abstract P192.

Reimer et al., 1998, "Povidone-iodine liposomes—Development of a novel anti-infective for topical treatment," J. Hosp. Infect. 40(Supp. A): Abstract P.9.2.7.

Reimer et al., 1997, "Povidone-iodine liposomes—and overview," Dermatology 195(Suppl. 2):93-99.

Stratford et al., 1983, "Effects of topically applied liposomes on disposition of epinephrine and inulin in the albino rabbit eye," Int. J. Pharmaceutics 13:263-272.

Wutzler et al., "Comparative testing of liposomal and aqueous formulations of povidone-iodine for their angioirritative potential at the chorioallantoic membrane of ex ovo cultivated chick embryos," Dermatology 207(1):43-47.

Wutzler et al., 2002, "Virucidal activity and cytotoxicity of the liposomal formulation of povidone-iodine," Antiviral Res. 54:89-97.

Wutzler et al., 2001, "Virucidal activity and cytotoxicity of a liposomal formulation of povidone-iodine," 14th International Conference on Antiviral Research, Seattle, WA 36.988.

Wutzler et al., 2000, "Virucidal activity and cytotoxicity of a liposomal formulation of povidone-iodine," 7th Western Pacific Congress of Chemotherapy & Infectious Diseases, Dec. 11-14, Hong Kong.

Wutzler et al., 2000, "Virucidal and chlamydicidal activities of eye drops with povidone-iodine liposome complex," Ophthalmic Res. 32:118-125.

Seagrave, 2002, "Introduction to Remodeling and Repair in Respiratory Diseases" Chest the Cardiopulmonary and Critical Care Journal, 122:271S.

Edwards, et al., 1997, "Large Porous Particles for Pulmonary Drug Delivery", Science 276:1868-1871.

Giannelli, et al., 2003, "Tissue remodeling in Liver disease" Histology Histopathol 18:1267-1274.

Forneff-Lipp, et al., 2002, "List of disinfection procedures tested according to the "Guidelines for Testing Chemical Disinfectants" and found effective by the German Society for the decontamination of hands and hygienic handwash)".

Xiaonan Cia, 1994, "The Clinical Use and Dosage Form of Iodophors", Bulletin of the Medical School of Shantou University (2):77-89 (in Chinese and English).

Lineaweaver et al., 1985, Arch Surg 120:257-270.

Kallenberger et al., 1991, Hyg & Med 16:383-395.

* cited by examiner

PREPARATIONS FOR THE APPLICATION OF ANTI-INFECTIVE AND/OR ANTI-INFLAMMATORY AGENTS

The present application is the national stage application of International Application No. PCT/EP00/04782 filed May 25, 2000 (published as WO 00/72822 on Dec. 7, 2000 in English), which claims the benefit of German Application No. DE 19924312 filed May 29, 1999.

The invention concerns a process for the manufacture of preparations for the application of agents with anti-infective and/or anti-inflammatory properties to external or internal parts of the human or animal body in functional and cosmetic tissue remodelling and repair treatments.

Furthermore, the invention concerns a corresponding method of treatment, by applying a pharmaceutical preparation.

The use of anti-infective and anti-inflammatory agents is well known and a large number of pharmaceutical preparations with anti-infective and/or anti-inflammatory effect have been described in the art.

Such preparations are typically used to prevent or treat infectious maladies caused by microorganisms and viruses.

Thus, a plurality of different antibiotic and antiseptic agents are known for the topical treatment of infectious maladies. A plurality of antiseptic agents are known to serve as disinfectants in order to prevent such infectious maladies, and are applied in the treatment of wounds, in pre-operation scenarios etc.

Generally, antibiotics are preferred for applications in the body interior, whereas there appears to be some reluctance in the art of use antiseptic agents, specifically disinfectants, other than in external applications.

In the prior art, pharmaceutical preparations are known which comprise at least one anti-infective or anti-inflammatory agent combined with a suitable carrier, such as a liposome.

The use of antiseptics and/or wound-healing promoting agents for external application to humans and animals is disclosed in our earlier patent EP 0 639 373. Specifically, liposome preparations of PVP-iodine are shown therein to be topically applicable to the external parts of the eye. These preparations generally take the form of a cream, an ointment, a lotion, a gel or a drop formulation.

It should be understood that alternative drug carriers of a similarly particulate character exist. These drug carriers can often—and also in the context of this invention—be used instead of liposomes and include microspheres (generally comprising lipophilic polymers), nanoparticles, "Large Porous Particles" and individually coated drug substance molecules, e.g. made by using pulsed laser deposition (PLD) techniques. These PLD methods can be used to apply coatings to drug powders and to modify surface properties and release rate to a variety of drug systems.

Where hereinafter reference is made to liposomes or particulate carriers, it is to be understood that this is to incorporate such alternative carriers, too.

Body tissues can be damaged by a broad variety of causes. Thus, wounds can be caused by the contact of the human or animal body with an object such as a weapon, a tool, a vehicle etc. The skin can be damaged by exposure to heat or other types of radiation, or to aggressive chemicals etc. Body tissues can be damaged by infective diseases caused by microorganisms or viruses.

The generation of new body tissue, which is the main activity in tissue repair processes, can sometimes itself have a negative effect. This negative effect can be functional, in that the repaired or regrown tissue doesn't reach the performance characteristics of the destroyed tissue which it replaces. Sometimes, the negative effect can be cosmetic, in that the regrown or repaired tissue is perceived to be ugly or disfiguring. Of course, these effects can appear in combination.

Thus, tissue repair can result in scar tissue formation, which can render a body part less elastic or resilient, or can leave a cosmetic disfiguration. This is not restricted to the external skin of the body; scar tissue can also lead to a deteriorated functionality of mucosa and other body tissues, including the internal organs of the body.

Corresponding types of undesired tissue repair effects are hyperkeratosis and unregulated proliferation of tissue.

Other problems arise, often after infective diseases or surgery, in the formation of neoplasms, intergrowth, etc.

The need for control of such effects in the treatment of diseases, wounds, burns etc. has recently become the object of much attention. Thus, it is now generally excepted that remodelling of the damaged tissue, to reconstitute as much of the original functionality and cosmetic effect as possible, is necessary and desirable.

This applies both to the external, visible parts of the human and animal body, as to the internal parts and organs of such bodies.

It has now surprisingly been found that the application of anti-infectiva and anti-inflammatory agents, to body parts where tissue repair takes place, has a very beneficial effect in avoiding the formation of undesired tissue. Functional and cosmetic restitution of the tissue proceeds easier and with less disturbance under the influence of anti-infectiva and anti-inflammatory agents.

This is specifically so where the anti-infectiva and anti-inflammatory agents are applied in the form of a pharmaceutical preparations wherein they are combined with a suitable carrier.

It is an object of the instant invention to provide a pharmaceutical preparation, and a corresponding treatment method, which can be used in functional and cosmetic remodelling and repair treatments of human and animal body tissues, to restore the original function and appearance of the tissue.

It is another related object of the instant invention to provide such preparations and methods which can be used to suppress the occurrence of undesired tissue formation in body part healing processes which involve the formation or regrowth of new body tissues.

According to the invention these objectives are attained by the feature combinations of the independent patent claims. In particular, the invention provides a method of functional and cosmetic tissue remodelling and repair in the human or animal respiratory tract, by applying, to said tract, a pharmaceutical preparation comprising at least one anti-inflammatory especially antiseptic and/or wound-healing promoting agent combined with a particulate carrier.

Advantages and embodiments of the invention are defined in the attached dependent claims.

In the context of this invention, an anti-infective agent is any agent known in the art which has an anti-infective efficiency and is pharmaceutically acceptable for the intended application.

Anti-inflammatory agents in accordance with this invention broadly include antibiotic and antiviral preparations, and more specifically comprise antiseptic agents, antibiotic agents, corticosteroids etc.

In the context of this invention, antiseptic agents are understood to include those disinfecting agents which are pharmaceutically acceptable and suitable for the treatment of the respective intended body part, the extent that they can be formulated in accordance with the invention.

More specifically, antiseptic agents include inter alia oxygen- and halogen-releasing compounds; metal compounds, e.g. silver and mercury compounds; organic disinfectants including inter alia formaldehyde-releasing compound, alcohols, phenols including alkyl- and arylphenols as well as halogenated phenols, quinolines and acridines, hexahydropyrimidines, quaternary ammonium compounds and iminium salts, and guanidines. Phenol derivatives include thymol, eugenol, and hexachlorophene.

Wound-healing agents comprise agents promoting granulation and epithelization such as dexpanthenol, allantoines, azulenes, tannines, and vitamine B-type compounds.

The invention is premised on the surprising fact that particulate carriers, especially liposomes, but also microspheres, nanoparticles Large Porous Particles and coated drug substance molecules, are highly suited as carriers for anti-infective and anti-inflammatory agents, especially for antiseptics such as povidone iodine, for the uses envisaged here.

The preparations according to this invention permit protracted release of the agent or agents, and provide an extended and topical activity at the desired locus of action by interaction with cell surfaces.

The anti-infective and/or anti-inflammatory preparation can be administered by known methods. For example, a liposome preparation can be made by loading liposomes with PVP iodine in a conventional procedure.

The nature or constitution of the liposomes is generally not critical. The liposome preparation as, for example, described in EP 0 639 373 can be administered in the various forms shown therein. The disclosure of EP 0 639 373 is incorporated by reference.

The preparations according to this invention apparently do not only contain the active agent, like povidone iodine, encapsulated in the particulate carrier, especially in liposomes. It seems that there is also some amount of agent which is not contained inside the carrier. The preparations according to the invention often show a marked initial effect which is observed in addition to the slower, protracted release of the active agent from the carrier. This effect is especially observed where the carrier comprises liposomes. Without wishing to be bound to any theoretical explanation, it is presently assumed that in addition to active agent encapsulated inside the liposomes, some active agent is present outside of the liposomes, and probably loosely bound to the outer surfaces of the liposomes. This could be due to association of active agent molecules with the liposomal membrane, or it could be due to active agent molecules forming a layer on the liposomal surface, which layer partly or even fully coats the liposome externally. The type and amount of this initial agent effect can e.g. be influenced by choice of the concentration parameters.

The amphiphilic substances generally known in prior art to form liposome membranes can be employed in the context of the invention as long as they are pharmaceutically acceptable for the intended application. Presently, liposome forming systems comprising lecithin are preferred. Such systems can comprise hydrogenated soy bean lecithin besides cholesterol and disodium succinate-hexahydrate; it is presently specifically preferred to use hydrogenated soy bean lecithin as the sole membrane-forming agent.

The known prior art methods for forming liposome structures are described in the documents cited above and can generally be used in the context of the invention. Broadly, these methods comprise mechanical agitation of a suitable mixture containing the membrane forming substance and water or an aqueous solution. Filtration through suitable membranes is preferred in forming a substantially uniform liposome size.

The average size of the liposomes according to this invention can vary over a broad range, generally from about 1 to about 20000 nm. Liposomes with diameters in the range of about 50 and 4000 nm are preferred. Liposomes with diameters at around 1000 nm are presently most preferred for e.g. gel applications. For solutions, small average diameters may be more suitable. In one embodiment, the liposomes are of substantially uniform size, in the range between about 20 and 30 μm diameter for application to the trachea, in the range between about 10 and 20 μn diameter for application to the bronchi and between about 1 and 5 μm, preferably between about 3 and 5 μm diameter for application to the alveoli.

Where alternative particulate carriers are used, they are generally prepared as known in the art. Thus, microspheres which are used to deliver a very wide range of therapeutic or cosmetic agents, are made as described for example in WO 95/15118.

Nanoparticles may in some cases be used, provided that they can be loaded with a sufficient amount of active agent and can be administered according to this invention. They can be prepared according to the methods known in the art, as e.g. described by Heyder (GSF München) in "Drugs delivered to the lung, Abstracts IV, Hilton Head Island Conference, May 1998.

Methods using a pulse laser deposition (PLD) apparatus and a polymeric target to apply coatings to drug powders in a short non-aqueous process are also suitable for the formation of particulate preparations according to this invention. These have e.g. been described by Talton et al., "Novel Coating Method for Improved Dry Delivery", Univ. of Florida UF 1887 (1998).

A further suitable delivery system employs "Large Porous Particles" as disclosed by David A. Edwards et al. in "Large Porous Particles for Pulmonary Drug Delivery" (Science, 20. June 1997, Vol. 276, p. 1868-1871).

Preferred anti-inflammatory agents comprise antiseptic agents, antibiotics, corticosteroids and wound-healing promoting agents, as single substances or in combination with each other.

Preferred antiseptic agents comprise the well-known pharmaceutical substances providing fast effect, a broad range of activity, low systemic toxicity and good tissue compatibility. They can e.g. be selected from the group comprising metal compounds, phenolic compounds, detergents, iodine and iodine complexes. A specifically preferred antiseptic agent is povidone iodine.

Some presently highly preferred embodiments of the invention comprise anti-inflammatory agents or combinations of such agents which show beneficial effects in tissue repair, especially with respect to functional and cosmetic tissue remodelling. In these embodiments, the active agent is often an antiseptic, such as PVP-iodine, or an antibiotic.

In preferred embodiments, the invention's preparations containing anti-inflammatory agents may further comprise wound-healing promoting agents known to promote epithelisation. These include vitamins, specifically from the vitamin B group, allantoin, some azulenes etc., and further agents such as anaesthetic agents. Inventive preparations can also contain customary further agents, including adjuvants and additives, antioxidants, conserving agents or consistency-forming agents such as viscosity adjusting additives, emulgators etc.

Generally, the concentrations in the preparation, particle sizes, active agent loadings etc. will be selected for such alternative carriers to correspond basically to the parameters discussed herein with respect to liposome preparations. Selecting and providing such parameter based inter alia on straightforward experimentation, is well within the skill of an ordinary worker experienced in this art.

Preparations according to this invention can take a variety of forms, including solutions, dispersions, lotions, creams, ointments gels and wound dressings (e.g. gauzes).

Generally, the amount of active agents in an inventive preparation will be determined by the desired effect on the one hand and the carrying capacity of the carrier preparation for the agent on the other hand.

Broadly, a solution or dispersion of active agent in an inventive liposome preparation can range between the lower limit of effectiveness of the agent and the solubility or dispersability limit of the agent in the respective solvent or dispersant.

Similar considerations broadly limit the amount of agent in lotions, creams, ointments or gels, or any other such preparation.

More specifically, for an antiseptic such as povidone iodine, a solution or dispersion in an inventive liposome preparation can contain between 0.1 and 10 g of agent in 100 g of preparation. Such a preparation will then typically contain between 1 and 5 g of liposome membrane forming substance especially lecithine per 100 g of preparation.

In a lotion, which can be a hydrophilic or a lipophilic lotion, a typical range of active agent will be between 0.5 and 10 g agent, and between 3 and 8 g, preferably about 5 g of liposome membrane forming agent such as hydrogenated soy bean lecithins, per 100 g of lotion. In the case of a hydrophilic lotion, electrolyte solution will often be used in preparing the liposome containing lotion. A lipophilic lotion will often be made from agent, membrane forming substance and lipophilic formation agents such as medium chain length triglycerides etc.

A hydrophilic cream comprising an inventive liposome preparation will generally comprise between 0.1 and 10 g agent, such as povidone iodine, together with between about 1 and 10 g membrane forming substance and further typical O/W cream forming additives, per 100 g of cream.

A comparable amphiphilic cream according to the invention will have similar contents of agent and membrane forming substance such as lecithins, and will have the typical further additives of an amphiphilic cream.

A hydrophilic ointment according to the invention can broadly comprise between 0.1 and 10 g agent and between 1 and 10 g liposome membrane forming substance such as lecithine, together with typical prior art ointment basis substances such as Macrogol™ and water, in 100 g of ointment.

A non-alcoholic hydrogel according to the invention could broadly comprise between 1 and 5 g agent such as povidone iodine, approximately 2 g lecithine and gel forming substances such as Carbopol™, with pH-adjusting agent and water to form 100 g of hydrogel.

One presently preferred delivery system is a wrap, plaster or band coated or otherwise provided with the inventive preparation, especially a liposomal PVP-iodine solution, dispersion, gel, cream or ointment.

More specific formulations are notable from the embodiment example.

The features and advantages of this invention will become notable in more detail from the ensuing description of preferred embodiments. In these embodiments which include a best mode, povidone iodine is exemplified as an antiseptic agent. This should, however, not be construed as a restriction of this invention to antiseptic agents or, among antiseptic agents, to povidone iodine, although such preparations are specifically preferred.

One preferred method for producing the invention's liposomes can generally be described as follows:

The lipid membrane forming components, e.g. lecithine, are dissolved in a suitable solvent such as chloroform or a 2:1 mixture of methanol and chloroform and are filtered under sterile conditions. Then, a lipid film is produced on a sterile high surface substrate, such as glass beads, by controlled evaporation of the solvent. In some cases, it can be quite sufficient to form the film on the inner surface of the vessel used in evaporating the solvent, without using a specific substrate to increase the surface.

An aqueous system is prepared from electrolyte components and the (one or more) active agents to be incorporated in the liposome preparation. Such an aqueous system can e.g. comprise 10 mmol/l sodium hydrogen phosphate and 0.9% sodium chloride, at ph 7.4; the aqueous system will further comprise at least the desired amount of the active agent, which in the embodiment examples is povidone iodide. Often, the aqueous system will comprise an excess amount of agent or agents.

The liposomes are generally formed by agitating said aqueous system in the presence of said film formed by the lipid components. At this stage, further additives can be added to improve liposome formation; e.g. sodium cholate can be added. Liposome formation can also be influenced by mechanical action such as pressure filtration through e.g. polycarbonate membranes, or centrifuging. Generally, the raw liposome dispersion will be washed, e.g. with electrolyte solution as used in preparing the above-described solution of the active agent.

When liposomes with the required size distribution have been obtained and washed, they can be redispersed in an electrolyte solution as already described, often also comprising sugars such as saccharose or a suitable sugar substitute. The dispersion can be freeze-dried, and it can be lyophilysed. It can, prior to use, be reconstituted by addition of water and suitable mechanical agitation at the transition temperature of the lipid component, which for hydrogenated soy bean lecithine is e.g. 55° C.

In the following Examples, hydrogenated soy bean lecithine (EPIKURON™ 200 SH obtainable from Lukas Meyer, Germany or PHOSPOLIPON™ 90H obtainable from Nattennann Phospholipid GmbH, Germany) was used. However, other pharmaceutically acceptable liposome membrane forming substances can be used instead, and the person skilled in the art will find it easy to select suitable alternative liposome forming systems from what is described in prior art.

EMBODIMENT EXAMPLE I

In a 1000 ml glass flask, provided with glass beads for increased surface, 51.9 mg cholesterol and 213 mg hydrogenated soy bean lecithins were dissolved in a sufficient amount of a mixture of methanol and chloroform in a 2:1 ratio. The solvent was then evaporated under a vacuum until a film was formed on the inner surface of the flask and on the glass beads.

2.4 g PVP-iodine (containing about 10% available iodine) were separately dissolved in 12 ml water.

Again in a separate vessel, 8.77 g sodium chloride and 1.78 g Na$_2$HPO$_4$.2H$_2$O were dissolved in 400 ml water. Further water was added up to a total volume of 980 ml, and then, approximately 12 ml 1N hydrochloric acid were added to adjust pH to 7.4. This solution was then topped up with water to exactly 1000 ml.

In a fourth vessel, 900 mg saccharose and 57 mg disodium succinate were dissolved in 12 ml water.

The PVP iodine solution was then added to the lipid film in the flask and the mixture was shaken until the film dissolved. This produced liposome formation from the hydrated lipids in the flask. The product was centrifuged and the supernatant liquid was discarded. The saccharose solution was added ad 12 ml and the product was again centrifuged. Afterwards the supernatant liquid was again discarded. At this stage, a further washing step, using the saccharose solution or the sodium chloride buffer solution could be used.

After the last centrifugation step and discarding of the supernatant, sodium chloride buffer solution was added ad 12 ml, and the liposomes were homogenously distributed therein.

The product was then distributed into vials each containing 2 ml liposome dispersion, and the vials were then subjected to a freeze-drying step.

After the freeze-drying, each vial comprised about 40 mg solids.

The method of Embodiment Example I has a minor disadvantage in that the PVP iodine solution used, due to the high percentage of solids, is rather viscous and thus more difficult to handle.

EMBODIMENT EXAMPLE II

In a 2000 ml flask provided with glass beads to increase surface, 173 mg hydrogenated soy bean lecithine and 90 mg disodium succinate were dissolved in approximately 60 ml of a methanol/chloroform mix in a 2:1 ratio. The solvent was removed under vacuum until a film was formed.

4 g PVP iodine (10% available iodine) were dissolved in 40 ml of the sodium chloride buffer solution described in Embodiment Example I, and were added to the lipid film in the flask. The flask was then shaken until the film dissolved and liposomes were formed.

The product was centrifuged and the supernatant liquid was discarded.

To the thus produced liposome pellet, further sodium chloride buffer solution was added ad 40 ml, and the centrifuging step was repeated. The supernatant was again discarded. At this stage, this washing step could be repeated where necessary.

After the final centrifuging and decanting step, sodium chloride buffer solution was again added to the precipitated liposomes ad 40 ml. The homogenous dispersion was then distributed into vials, each vial containing about 2 ml liposome dispersion, and the vials were then subjected to a freeze-drying step. This produced approximately 200 mg freeze-dried solids per vial.

From the freeze-dried solids of Examples I and II, further preparations were made as described in subsequent Embodiment Examples and Test Reports.

Like that of Embodiment Example I, the above-described method uses a hydrating step after film formation in the presence of organic solvents and aims at inclusion rates of 5 bis 15%. These methods generally produce rather large and often multi-lamellar liposomes.

The above-described methods can be modified by a high pressure filtering step through a suitable membrane such as a polycarbonate membrane after the raw liposomes have been formed or after any of the subsequent washing steps or directly by using high pressure homogenisation. This produces much smaller, unilamellar liposomes at increased amounts of encapsulated agent.

Instead of high pressure homogenisation, other prior art methods known to provide small uniform sized liposomes can be employed.

EMBODIMENT EXAMPLE III

A hydrophilic (O/W) cream was prepared from 10 g hydrogenated soy bean lecithine/PVP iodine liposomes as described in Embodiment Example II; these were mixed with 4 g Polysorbate 40™, 8 g cetylstearyl alcohol, 8 g glycerol, 24 g white vaseline, and water ad 100 g.

EMBODIMENT EXAMPLE IV

An amphiphilic cream was prepared from 10 g hydrogenated soy bean lecithine/povidone iodine liposomes as described in Embodiment Example II; 7.5 g medium chain length tryglyceride, 7 g polyoxyethyleneglycerol monostearate, 6 g cetylstearyl alcohol, 8 g propylene glycol, 25 g white vaseline, and water ad 100 g.

EMBODIMENT EXAMPLE V

A hydrophilic ointment which can be rinsed off with water was prepared using 10 g of liposomal PVP iodine as described in Embodiment Example II, 55 g Macrogol 400™, 25 g Macrogol 4000™, and water ad 100 g.

EMBODIMENT EXAMPLE VI

A hydrogel was prepared from 4 g liposomal PVP iodine as described in Embodiment Example II, 0.5 g Carbopol 980 NF™, sodium hydroxide ad pH 7, water ad 100 g.

Further modifications of the above-described embodiments are envisaged.

Thus, the creams of Embodiment Examples III and IV can have an additional content of an agent known to promote the healing of wounds, such as allantoin. Such an agent will be added in a pharmaceutically useful concentration, in the case of allantoin in the range of 0.1 to 0.5 g, per 100 g of cream. The wound healing agent can be incorporated in the cream base, in which case it will largely be outside the liposomes. It can, however, be partly or mostly incorporated in the liposomes, in which case it will be added at a corresponding suitable stage of the liposome preparation method.

Similar alternatives are easily envisaged on the basis of the further Embodiment Examples.

It is also possible to prepare embodiments similar to the above described ones, which comprise an anti-infective and/or anti-inflammatory agent which is not an antiseptic agent as e.g. povidone iodine disclosed in the above Embodiment Examples. Thus, an antibiotic agent or a corticosteroid can e.g. be used.

For application of the inventive preparations to a patient, known systems can be used, such as pneumatic pump applicators, two-chamber gas pressure packs etc.

In a pneumatic pump applicator, a bellows device is provided between an upstream and a downstream valve, both valves operating one way in the same direction. A supply of pharmaceutical preparation, such as an ointment or gel, is contained in a reservoir upstream of the valves-and-bellows device.

When compressing the bellows, the downstream valve opens and permits a dosed amount of preparation to leave the device for application. When the bellows is extended, this valve shuts and prevents reentry of the preparation. At the same time, the upstream valve opens and permits preparation from the reservoir to enter into the bellows, for release through the downstream valve upon the next compression step of the bellows.

The reservoir is sealed by a closure element which can move through the reservoir like a piston moves in a cylinder. By the stepwise emptying of the reservoir, this closure element is sucked into the reservoir, so that the remaining amount of pharmaceutical preparation in the reservoir is always sealed off, while at the same time the reservoir can be emptied.

Such a device is useful for pasty preparations, creams, ointments etc.

In a two-chamber gas pressure pack, the pharmaceutical preparation is contained in a bag of flexible plastics film material. Often, this is high pressure polyethylene.

The bag is contained inside a gas tight pressure vessel which further contains a supply of pressurizing gas, very often a compressed inert gas like nitrogen or air.

The plastic film bag has only one outlet, which is gas-tightly connected to the interior wall of the pressure vessel, surrounding a single opening thereof. The pressurized gas in the vessel tends to compress the bag, driving the pharmaceutical preparation inside the bag out through the opening of the bag and thus through the opening of the vessel. A valve and, in case, spray-head device is provided in the vessel mouth. Operating the valve releases a spray mist, a jet of liquid or a portion of flowable solid such as cream. Using such a system, solutions, emulsions, creams, ointments and gels can be dosed and applied.

Using inventive preparations efficiency and acceptability tests were then carried out, as follows:

Test I

This was an in-vitro-test of the bactericidal effect provided by an inventive povidone iodine liposome preparation. The test was based on the quantitative suspension test as described in "Richtlinien der Deutschen Gesellschaft für Hygiene und Mikrobio-logie", 1989. In this test, the bactericidal agent is used to kill *staphylococcus aureus* (ATCC 29213), a major problem in hospital hygiene.

The liposome preparation used was that of Embodiment Example I. At different contact times between 1 und 120 minutes, the minimum concentration of the preparation in water was determined which was capable of killing the staphilococci.

The results are shown in Table 1.

TABLE I

| Contact Time (Minutes) | Bactericidal Concentration |
| --- | --- |
| 1, 2, 3, 4 | ≧0.060% |
| 5, 30, 60 | ≧0.015% |
| 120 | ≧0.007% |

The results show that at short contact times (between 1 and 4 minutes) the bactericidal concentration is as low as 0.06% and that at long contact times (120 minutes) the bactericidal concentration can be as low as 0.007%.

Test II

The second test was a placebo-controlled clinical study of the local acceptability (at the eye) of an inventive povidone iodine liposome preparation. An eyedrop formulation was made using the liposomes of Embodiment Example I. It was tried on 15 male test persons. The inventive preparation was always used on one eye of the test person, with physiological sodium chloride solution added as a comparison to the respective other eye.

Specifically, each test person received one drop of PVP iodine liposome preparation in the right eye and one drop of physiological sodium chloride solution in the left eye, and this was twice repeated at hourly intervals. After 5, 30, 65, 95, 125 and 150 minutes as well as after 24 hours after the first application, symptoms were determined. These symptoms included hyperaemia, as measured with a slit/lamp microscope; burning; itching, and tear flow. Each symptom was measured according to a 4 point score with 0 corresponding to no symptom, 1 corresponding to a low degree, 2 corresponding to a medium degree and 3 corresponding to a strong degree of symptom appearance.

A sum score was calculated from the degree scores of all four symptoms and the 7 determination time points. The sum score could thus vary between 0 (=0 times 0 times 0) and 84 (=4 times 3 times 7).

The test persons were between 21 and 36 years old, with an average of 30 years of age. All test persons were healthy and not under medication during the test. Specifically, any illnesses of the eye and of the thyroid were excluded.

One test person was not evaluated for sum score since one control of symptoms after 150 minutes was missed.

The results are notable from Table II.

Overall, the sum score on both eyes was extremely low. It is surprising that on average, the sum score for the eyes treated with the povidone iodine liposome preparation was even lower than that for the eyes receiving physiological sodium chloride solution.

TABLE II

| Sum score | PVP-I-Liposomes Number of test persons | Phys. NaCl-Solution |
| --- | --- | --- |
| 0 | 11 | 6 |
| 1 | 3 | 6 |
| 2 | 0 | 2 |
| 3-84 | 0 | 0 |
| Average | 0.21 | 0.71 |
| Standard Deviation | 0.43 | 0.73 |
| Median | 0 | 1 |
| p-Value | 0.02 | |

11 test persons treated with the invention's povidone iodine liposome preparation showed no symptoms whatsoever. Three test persons had slight hyperaemia, one felt some very slight burning (this is the above-mentioned test person who could not be evaluated for some score). On the contrary, only six test persons exhibited no symptoms after receiving physiological sodium chloride solution. Four test persons experienced burning, one of them at two subsequent time points. One test person experienced slight burning and itching of the left eye. A total of four test persons showed some hyperaemia.

Test III

The virucidal and chlamydicidal activity of liposomal PVP-iodine has been studied, in cell cultures, by Wutzler et al., 9th European Congress for Clinic Microbiology and Infection Diseases, Berlin, March 1999. (Compare Wutzler et al. in: Ophtalmic Res. 2000; 32; 118-125). In cell cultures, liposomal PVP-iodine is highly effective against herpes simplex virus type 1 and adenovirus type 8, while the long-term cytotoxicity experiments indicated that the liposomal form is better tolerated than aqueous PVP-iodine by the majority of cell lines tested. PVP-iodine in liposomal form is not genotoxic.

Test IV

A 3% PVP-iodine hydrogel liposomal preparation was compared with a 3% PVP-iodine ointment, where the active agent was not in liposomal form. The agent was applied to standardized in vitro cultures of rat skin and peritoneal explants, as a screening for tissue compatibility of skin and wound antiinfectives.

The growth rate of the cultured explants was studied after 30 minutes exposure and incubation with a test substance.

Again, the substantially better toleration of the liposomal preparation was clearly shown in the results, in terms of peritoneum growth rate and skin growth rate.

With the ointment, the peritoneum growth rate reached 85%, and the skin growth rate reached 90%; with the liposomal hydrogel formulation, the peritoneum growth rate was 96%, and the skin growth rate was 108%; these values are to be compared with 100% values in a control test using Ringer's solution as the agent.

The invention claimed is:

1. A method for suppressing undesired tissue formation at a site of tissue damage in the respiratory tract of a patient comprising administering to a patient in need thereof, an amount of liposomes sufficient to suppress undesired tissue formation at the site of tissue damage, said liposomes containing povidone iodine.

2. The method of claim 1, wherein the liposomes further contain an anti-inflammatory agent.

3. The method of claim 1, wherein the liposomes further contain an anesthetic.

4. The method of claim 1, wherein the liposomes further contain a conserving agent or an antioxidant.

5. The method of claim 1, wherein the liposomes have a diameter in the range from 20 µm to 30 µm.

6. The method of claim 1, wherein the liposomes have a diameter in the range from 10 µm to 20 µm.

7. The method of claim 1, wherein the liposomes have a diameter in the range from 1 µm to 5 µm.

8. The method of claim 1, wherein the liposomes have a diameter in the range from 3 µm to 5 µm.

9. The method of claim 1, wherein the liposomes comprise a liposome membrane forming substance that is present in an amount between about 1 to 5%, by weight, of the liposomes.

10. The method of claim 1, wherein the liposomes are lecithin liposomes.

11. The method of claim 1, wherein the liposomes contain about 0.1 to about 10% by weight povidone iodine.

12. The method of claim 11, wherein the liposomes contain about 3% by weight povidone iodine.

13. The method of claim 1, wherein the liposomes further contain an antibiotic.

14. The method of claim 1, wherein the liposomes further contain a corticosteroid.

15. The method of claim 1, wherein the patient is a human patient.

16. The method of claim 1, wherein the site of tissue damage is in the trachea.

17. The method of claim 1, wherein the site of tissue damage is in the bronchi.

18. The method of claim 1, wherein the site of tissue damage is in the alveoli.

* * * * *